United States Patent
Harris et al.

(10) Patent No.: US 11,249,058 B2
(45) Date of Patent: Feb. 15, 2022

(54) SIDE CHAMBER PROCESS MONITOR FOR ADSORPTIVE SEPARATION PROCESS

(71) Applicant: UOP LLC, Des Plaines, IL (US)

(72) Inventors: James W. Harris, Palatine, IL (US); Heather A. Fleitz, Chicago, IL (US); Gregory A. Ernst, Mount Prospect, IL (US); Chad A. Williams, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 67 days.

(21) Appl. No.: 16/793,522

(22) Filed: Feb. 18, 2020

(65) Prior Publication Data

US 2021/0255152 A1 Aug. 19, 2021

(51) Int. Cl.
| | | |
|---|---|---|
| C07C 7/11 | (2006.01) |
| B01J 20/281 | (2006.01) |
| G01N 30/74 | (2006.01) |
| B01D 53/02 | (2006.01) |
| G01N 30/86 | (2006.01) |

(52) U.S. Cl.
CPC ........... *G01N 30/48* (2013.01); *B01D 53/025* (2013.01); *C07C 7/11* (2013.01); *G01N 30/74* (2013.01); *G01N 30/8675* (2013.01); *B01D 2256/24* (2013.01); *B01D 2257/7027* (2013.01)

(58) Field of Classification Search
None
See application file for complete search history.

(56) References Cited

U.S. PATENT DOCUMENTS

| | | | |
|---|---|---|---|
| 3,040,777 A | 6/1962 | Carson et al. | |
| 3,422,848 A | 1/1969 | Liebman et al. | |
| 3,943,184 A * | 3/1976 | Rosback | B01J 20/186 585/828 |
| 4,021,499 A * | 5/1977 | Bieser | C07C 7/13 585/828 |
| 4,028,428 A * | 6/1977 | Neuzil | C07C 7/13 585/828 |
| 4,402,832 A | 9/1983 | Gerhold | |
| 4,478,721 A | 10/1984 | Gerhold | |
| 5,595,665 A | 1/1997 | Noe | |
| 2006/0199989 A1 | 9/2006 | Frey | |
| 2010/0076243 A1* | 3/2010 | Cheng | B01J 20/18 585/820 |
| 2013/0158332 A1 | 6/2013 | Rauch et al. | |
| 2013/0317210 A1* | 11/2013 | Oroskar | B01J 39/26 536/125 |
| 2014/0368810 A1 | 12/2014 | Hotier | |

FOREIGN PATENT DOCUMENTS

EP  2813840 A1  12/2014

OTHER PUBLICATIONS

International Search Report from corresponding PCT application No. PCT/US2021/017586 dated May 13, 2021.
Written Opinion from corresponding PCT application No. PCT/US2021/017586 completed Apr. 29, 2021.

* cited by examiner

*Primary Examiner* — Tam M Nguyen

(57) ABSTRACT

Processes and apparatus for analyzing fluid properties of a stream are described. The processes utilize a simulated moving bed system and a rotary valve. The processes involve sending a portion of the pump-around stream to a side chamber where the moisture content of the adsorbent in the side chamber or one or more fluid properties of the stream or both are measured using an analyzer specific to each fluid property.

17 Claims, 2 Drawing Sheets

SIDE CHAMBER PROCESS MONITOR FOR ADSORPTIVE SEPARATION PROCESS

BACKGROUND

Continuous separation processes are commonly used for the selective adsorption of para-xylene from a mixture of $C_8$ aromatics. Generally, the processes use a solid adsorbent that preferably retains the para-xylene in order to separate the para-xylene from the rest of the mixture. Often, the solid adsorbent is in the form of a simulated moving bed, where the bed of solid adsorbent is held stationary, and the locations at which the various streams enter and leave the bed are periodically moved. The adsorbent bed itself is usually a succession of fixed sub-beds or modules. The shift in the locations of the liquid input and output in the direction of the fluid flow through the bed simulates the movement of the solid adsorbent in the opposite direction. Moving the locations of the liquid input and output is accomplished by a fluid tracking device known generally as a rotary valve which works in conjunction with distributors located between the adsorbent sub-beds. The rotary valve accomplishes moving the input and output locations through first directing the liquid introduction or withdrawal lines to specific distributors located between the adsorbent sub-beds. After a specified time period, called the step time or hold period, the rotary valve advances one index to the next valve position and redirects the liquid inputs and outputs to the distributors immediately adjacent and downstream of the previously used distributors. Each advancement of the rotary valve to the next valve position is generally called a valve step, and the completion of all the valve steps is called a valve cycle. In one commercial process, the step time is uniform for each of the valve steps in a valve cycle, and is generally about 60 seconds or so. A typical process contains 24 adsorbent sub-beds, 24 distributors located between the 24 adsorbent sub-beds, two liquid input lines, two liquid output lines, and associated flush lines.

The principle liquid inputs and outputs of the adsorbent system consists of four streams, which are the feed, the extract, the raffinate, and the desorbent. Each stream flows into or out of the adsorbent system at a particular flow rate, and each rate is independently controlled. The feed, which is introduced to the adsorbent system, contains the para-xylene that is to be separated from the other components in the feed stream. The desorbent, which is introduced to the adsorbent system, contains a liquid capable of displacing feed components from the adsorbent. The extract, which is withdrawn from the adsorbent system, contains the separated para-xylene, which was selectively adsorbed by the adsorbent, and the desorbent liquid. The raffinate, which is withdrawn from the adsorbent system, contains other $C_8$ aromatic components of the feed that are less selectively adsorbed by the adsorbent, and desorbent liquid. There also may be associated flush streams introduced to and withdrawn from the adsorbent system. The four principal streams are spaced strategically throughout the adsorbent system and divide the sub-beds into four zones, each of which performs a different function.

Zone I contains the adsorbent sub-beds located between the feed input and the raffinate output, and the selective adsorption of the para-xylene takes place in this zone. Zone II contains the adsorbent sub-beds located between the extract output and the feed input, and the desorption of components other than the para-xylene takes place in this zone. Zone III contains the adsorbent sub-beds located between the desorbent input and the extract output, and the para-xylene is desorbed in this zone. Finally, Zone IV contains the adsorbent sub-beds located between the raffinate output and the desorbent input. The purpose of Zone IV is to prevent the contamination of the para-xylene with other components.

The common method used to monitor the moisture content of the adsorbent chambers has been to monitor the feed, desorbent, extract and raffinate stream moisture content as bulk fluids. Injection of a specific quantity of water to the desorbent is done to maintain the moisture level as some of the water is not returned when the extract and raffinate are purified and the desorbent in these streams is recycled back to the adsorbent chamber. However, the use of a bulk liquid moisture analyzer on only specific operating regions can only give general guidelines on the moisture in the bulk liquid. It does not allow measurement of the bulk liquid moisture content in all operating regions. More importantly, it does not allow measurement of the moisture content on the adsorbent in the adsorbent chamber.

Another common practice in the industry is to determine the compositional profile of the para-xylene simulated moving bed separation process either by on-line gas chromatography analysis, or by off-line laboratory analysis. The on-line gas chromatography analysis typically requires about 10 minutes per analysis, which is considerably greater than the usual step time of the rotary valve. Therefore, only selected valve positions can be sampled and analyzed. Generally, only Zone II near the extract output and Zone IV near the desorbent input are sampled and analyzed. The data provided by this on-line gas chromatography procedure is useful for detecting some process upsets, but unfortunately analyzing the composition of only two valve positions provides limited information regarding the performance of the separation process and is only minimally useful for precise separation process control.

A more thorough determination of the compositional profile of the para-xylene simulated moving bed separation process is accomplished using off-line laboratory gas chromatography analysis to determine the values of the concentrations of the components in the samples for each valve position in a valve cycle. The measured concentrations are then plotted versus their relative valve positions to form what is generally called a pump-around profile. Using the pump-around profile, the recovery purity of the para-xylene can be calculated and the degree of optimization of the separation may be assessed. From this, for example, needed changes in the step time and/or liquid stream flow rates may be determined and implemented. The drawbacks to assessing the separation process in this fashion are the time delay between sampling and delivery of the analytical results, where the latter are used to determine whether or what process changes should be made; the labor involved to manually collect the stream samples; and the personal exposure of the operator manually collecting the stream samples from the process. Since the analysis is performed off-line, the time delay may be from one to several days long and can lead to plant disruption. Because of these drawbacks, refiners generally only perform this procedure about once every six months or if there is a problem with the separation process.

Accordingly, it would be desirable to provide processes for determining the moisture content of the adsorbent and the pump-around profile of these systems to provide rapid and frequent analysis of the fluid properties with low system maintenance, requiring minimal operator time and labor, and without plant disruption.

DETAILED DESCRIPTION

Figure 1:
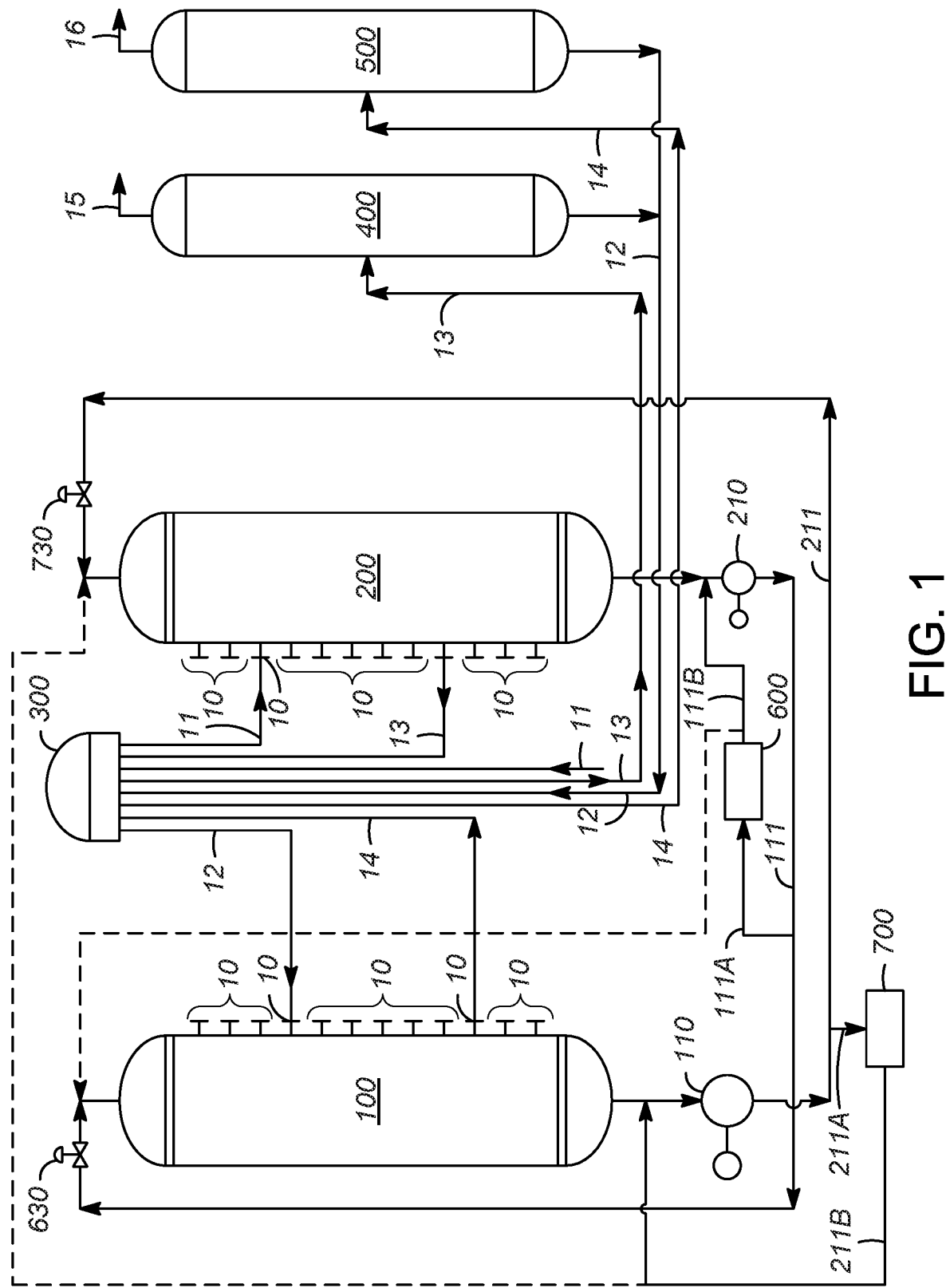
FIG. 1 is an illustration of one embodiment of the process of the present invention.

Adsorptive separation is applied to the recovery of a variety of hydrocarbon and other chemical products. Chemical separations using this approach which have been disclosed include the separation of mixtures of aromatics into specific aromatic isomers, of linear from nonlinear aliphatic and olefinic hydrocarbons, of either paraffins or aromatics from a feed mixture comprising both aromatics and paraffins, of chiral compounds for use in pharmaceuticals and fine chemicals, of oxygenates such as alcohols and ethers, and of carbohydrates such as sugars. Aromatics separations include mixtures of dialkyl-substituted monocyclic aromatics and of dimethyl naphthalenes. A major commercial application, which forms the focus of the prior references and of the following description of the present invention, without so limiting it, is the recovery of para-xylene and/or meta-xylene from mixtures of $C_8$ aromatics.

The invention normally is employed in an adsorptive separation process which simulates countercurrent movement of the adsorbent and surrounding liquid as described above, but it may also be practiced in a cocurrent continuous process, like that disclosed in U.S. Pat. Nos. 4,402,832 and 4,478,721. Processes for separating components of a feed stream are discussed in Chapter 10.3 of the Handbook of Petroleum Refining Processes, 3d Edition at pages 10.29-10.35, which is incorporated by reference herein.

Optimization of the process in the adsorbent section requires tight process control of many variables. Among those of particular interest are the method used to optimize and control the adsorbent chamber moisture (hydration) and the composition of the streams. The present method provides a better understanding of the hydration level at the adsorbent surface which will enable more precise control of the hydration level of the process. With tighter control, improved production results and extending the life of the adsorbent are possible.

In addition, the composition of the pump-around stream is currently monitored using a GC only during Zones II and IV. Increased information on composition of the pump-around stream allows optimization of the zone flow set points for more efficient operation of the process.

Additional properties can also be measured in the side chamber, including, but not limited to, analytical testing of the side chamber adsorbent or adsorbent fines feedback (delta P information).

Adding a side chamber system to the pump-around stream allows for the installation of a small volume of adsorbent that can be monitored at the ideal conditions for analysis. This may include IR or capacitance measurement at the surface of the adsorbent. As the side chamber conditions are further refined and compositional sensors are improved (e.g., microGC, GCxGC or spectral techniques), the compositional analysis direct optimization of each zone can be increased, further improving the overall operation of the process.

The side chamber system can be located with a high pressure source at the circulation pump discharge. The outlet from the side chamber system can be returned to the process at the pump suction or downstream at the outlet of the control valve.

One aspect of the invention is a process for analyzing fluid properties of a stream. In one embodiment, the process comprises: providing a simulated moving bed system comprising a plurality of adsorbent sub-beds in fluid communication with each other and with a rotary valve for separating one or more selectively adsorbed components from a feed stream comprising the one or more selectively adsorbed components and one or more non-selectively adsorbed components; rotating the rotary valve to a first valve position to direct the feed stream to a first sub-bed of the plurality of sub-beds; introducing a portion of a pump-around stream between two of the adsorbent sub-beds into a side chamber comprising an adsorbent; and measuring a moisture content of the adsorbent in the side chamber or at least one fluid property of the portion of the pump-around stream in the side chamber or both using an analyzer.

In some embodiments, the at least one fluid property comprises at least one of: a moisture content of the pump-around stream, a composition of the pump-around stream, or a concentration of a hydrocarbon species of the pump-around stream.

In some embodiments, the at least one fluid property is the composition of the portion of the pump-around stream and wherein the analyzer is a gas chromatograph.

In some embodiments, the at least one fluid property is the concentration of a hydrocarbon species in the portion of the pump-around stream and wherein the analyzer comprises a spectrometer.

In some embodiments, the at least one fluid property is the moisture content of the pump-around stream and wherein the analyzer comprises a moisture analyzer.

In some embodiments, the moisture content of the adsorbent is measured and wherein the portion of the pump-around stream is in direct contact with the adsorbent. In some embodiments, the analyzer is a moisture analyzer.

In some embodiments, the process further comprises: returning the portion of the pump-around stream from the side chamber to a remainder of the pump-around stream after measuring the at least one fluid property.

In some embodiments, the feed stream comprises $C_8$ aromatics and the selectively adsorbed component comprises para-xylene.

In some embodiments, rotating the rotary valve comprises rotating the rotary valve to a plurality of valve positions that each direct the feed stream to a different one of the sub-beds, and measuring the at least one fluid property is repeated for each of the plurality of valve positions to assess the at least one fluid property at each valve position.

In some embodiments, the number of the plurality of valve positions corresponds to a number of the plurality of sub-beds, wherein the number of the plurality of valve positions is 24 defining a full valve cycle, and wherein rotating the rotary valve comprises rotating the rotary valve for the full valve cycle, and measuring the at least one fluid property is repeated until the full valve cycle is completed.

Another aspect of the invention is a process for analyzing fluid properties of a stream. In one embodiment, the process comprises: providing a simulated moving bed system comprising a plurality of adsorbent sub-beds in fluid communication with each other and with a rotary valve for separating one or more selectively adsorbed components from a feed stream comprising the one or more selectively adsorbed components and one or more non-adsorbed components; rotating the rotary valve to a first valve position to direct the feed stream to a first sub-bed of the plurality of sub-beds; introducing a portion of a pump-around stream between two of the adsorbent sub-beds into a side chamber comprising an adsorbent and wherein the portion of the pump-around stream is in direct contact with the adsorbent; measuring a moisture content of the adsorbent using a moisture analyzer.

In some embodiments, the process further comprises: measuring at least one additional fluid property of the portion of the pump-around stream.

In some embodiments, the at least one additional fluid property comprises at least one of: a moisture content of the pump-around stream, a composition of the pump-around stream, or a concentration of a hydrocarbon species of the pump-around stream.

In some embodiments, the process further comprises: returning the portion of the pump-around stream from the side chamber to a remainder of the pump-around stream after measuring the property.

In some embodiments, the feed stream comprises $C_8$ aromatics and the selectively adsorbed component comprises para-xylene.

In some embodiments, rotating the rotary valve comprises rotating the rotary valve to a plurality of valve positions that each direct the feed stream to a different one of the sub-beds, and measuring the at least one fluid property is repeated for each of the plurality of valve positions to assess the at least one fluid property at each valve position.

Another aspect of the invention is a simulated moving bed system for separating one or more selectively adsorbed components from a feed stream comprising the selectively adsorbed component and one or more non-selectively adsorbed components. In one embodiment, the system comprises: a plurality of adsorbent sub-beds in fluid communication with each other and comprising two sub-beds in direct fluid communication with each other via a pump-around stream; a rotary valve in fluid communication with each of the plurality of sub-beds and configured to rotate to a plurality of valve positions that each direct the feed stream to a different one of the plurality of sub-beds; a side chamber in fluid communication with the pump-around stream; and an analyzer for a property in communication with the side chamber.

In some embodiments, the analyzer is selected from a moisture analyzer, a gas chromatograph, or a spectrometer.

In some embodiments, there are at least two analyzers in the side chamber.

FIG. 1 is a schematic diagram of a simulated-moving-bed adsorption process incorporating the present invention. The process sequentially contacts a feed inlet stream 11 with adsorbent contained in the vessels and a desorbent inlet stream 12 to separate an extract outlet stream 14 from a raffinate outlet stream 13. In the simulated-moving-bed countercurrent flow system, progressive shifting of multiple liquid feed and product access points downward through an adsorbent chamber simulate the upward movement of adsorbent contained in the chamber. The adsorbent in a simulated-moving-bed adsorption process is contained in multiple beds in one or more vessels; two vessels 100 and 200 in series are shown in FIG. 1. Each vessel contains multiple beds of adsorbent contacted through a number of access points 10 relating to the number of beds of adsorbent; the position of the feed inlet stream 11, desorbent inlet stream 12, extract outlet stream 14 and raffinate outlet stream 13 are shifted along the access points to simulate a moving adsorbent bed.

One method of cyclic advancement of the input and output streams through the fixed bed of adsorbent is a manifold system in which the valves in the manifold are operated in a sequential manner to effect the shifting of the input and output streams thereby allowing a flow of fluid with respect to solid adsorbent in a countercurrent manner. A preferred mode to effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. In the present scheme as shown in FIG. 1, a rotary disc type valve 300, as characterized for example in U.S. Pat. Nos. 3,040,777 and 3,422,848, incorporated herein by reference, effects the shifting of the streams along the adsorbent chamber to simulate countercurrent flow.

Coincident with this simulated upward movement of the solid adsorbent is the movement of the liquid occupying the void volume of the packed bed of molecular sieve. So that countercurrent contact is maintained, a liquid flow down the adsorbent chamber may be provided by a pump. Circulating liquid comprising desorbent, extract and raffinate circulates through the vessels through pumps 110 and 210, returning to the adsorbent chambers respectively via conduits 111 and 211. As an active liquid access point moves through a cycle, that is, from the top of the chamber to the bottom, the chamber circulation pump moves through different zones which require different flow rates. A programmed flow controller may be provided to set and regulate these flow rates. Systems to control the flow of circulating liquid are described in U.S. Pat. No. 5,595,665, but the particulars of such systems are not essential to the present invention.

The principal streams involved in simulated-moving-bed adsorption as illustrated in FIG. 1 may be characterized as follows. A "feed stream" is a mixture containing one or more extract components and one or more raffinate components to be separated by the process. The "extract product" comprises the recovered desired component, such as para-xylene or meta-xylene having a defined purity, after recovery which usually comprises fractionation. The "extract stream" comprises a component, usually the desired product which is more selectively adsorbed by the adsorbent, along with accompanying desorbent material. The "raffinate product" comprises components, after removal of the extract product, which are less selectively adsorbed. The "raffinate stream" comprises raffinate product, along with desorbent, before fractionation. "Desorbent" refers to a material capable of desorbing an extract component, which generally is inert to the components of the feed stream and easily separable from both the extract and the raffinate.

The extract product has a purity generally defined with respect to raffinate components. For example, para-xylene product impurities may comprise other $C_8$ aromatics, such as ethylbenzene, meta-xylene and ortho-xylene optionally along with nonaromatics and lighter and heavier components. Meta-xylene purity accordingly would relate to the sum of the amounts of ethylbenzene, para-xylene and ortho-xylene. The product should be of at least 99 weight-% purity according to this standard, i.e., at least a ratio of 99 extract to 1 of impurities. Preferably the weight ratio is at least 995 extract to 5 of impurities, and often at least 999 to 1. When recovering para-xylene, the purity may reflect a weight ratio to other $C_8$ aromatics of 9999 to 1 or more.

The extract outlet stream 14 and raffinate outlet stream 13 from the illustrated scheme contain desorbent in concentrations relative to the respective product from the process of between 0% and 100%. The desorbent generally is separated from raffinate and extract components by conventional fractionation in raffinate column 400 and extract column 500 as illustrated in FIG. 1 and returned to the process in desorbent inlet stream 12. Each of the raffinate and extract columns comprise appurtences for condensing and separating the overhead stream and supplying heat to the bottom of the column as known in the art.

FIG. 1 shows the desorbent as bottoms from the respective column, implying that the desorbent is heavier than the extract or raffinate. The extract product 16 and raffinate product 15 from the process are recovered from the extract outlet stream 14 and the raffinate outlet stream 13 in the respective columns; the extract product from the separation of $C_8$ aromatics usually comprises principally one or both of para-xylene and meta-xylene, with the raffinate being principally non-adsorbed $C_8$ aromatics and ethylbenzene.

The positions of the input and output streams define operational zones which are useful in understanding the present invention. The adsorption zone is defined as the adsorbent located between the feed inlet stream 11 and the raffinate outlet stream 13. In this zone, the feedstock contacts the molecular sieve, an extract component is retained, and a raffinate stream is withdrawn. Since the general flow through this zone is from the feed stream which passes into the zone to the raffinate stream which passes out of the zone, the flow in this zone is considered to be a downstream direction when proceeding from the feed inlet stream 11 to the raffinate outlet stream 13.

Immediately upstream with respect to fluid flow in adsorption zone I is the purification zone, defined as the adsorbent between the extract outlet stream 14 and the feed inlet stream 11. The basic operations taking place in the purification zone are the displacement from the non-selective void volume of the adsorbent of any raffinate material carried into this zone and the displacement of any raffinate material retained within the selective pore volume of the molecular sieve. Purification is achieved by passing a portion of extract stream material leaving the desorption zone into the purification zone's upstream boundary to effect the displacement of raffinate material. The flow of liquid in the purification zone is in a downstream direction from the extract outlet stream 14 to the feed inlet stream 11.

Immediately upstream of the purification zone with respect to the fluid flow is the desorption zone. The desorption zone is defined as the adsorbent between the desorbent inlet stream 12 and the extract outlet stream 14. The function of the desorption zone is to allow a desorbent which passes into this zone to displace the extract component retained in the adsorbent during previous contact with feed in the adsorption zone in a prior cycle of operation. The flow of fluid in the desorption zone is essentially in the same direction as that of the prior zones.

The buffer zone is defined as the adsorbent between the raffinate outlet stream 13 and the desorbent inlet stream 12 and is located immediately upstream with respect to the fluid flow to the desorption zone. This zone is utilized to conserve the amount of desorbent utilized in the desorption step since a portion of the raffinate stream which is removed from the adsorption zone can be passed into the buffer zone to displace desorbent present in that zone into the desorption zone. This zone contains enough desorbent to prevent raffinate material present in the raffinate outlet stream 13 from passing out of the adsorption zone into the buffer zone and further from passing into the desorption zone thereby contaminating the extract stream removed from the purification zone.

Different commercial units for the separation of $C_8$ aromatics employ either light or heavy desorbents. If the desorbent was lighter than the extract or raffinate, the desorbent would be recovered from the overhead while the extract or raffinate would be the bottoms stream, as would be understood by those of skill in the art.

A portion 111A of the circulating liquid comprising desorbent, extract and raffinate from conduit 111 (pump-around stream) is sent to a side chamber 600 which contains adsorbent. The sample composition changes as the feed and all other ports change in the main chambers. This sample to be analyzed is a very small portion only as necessary to make the composition measurement and will be typically less than 10 gallons per minute (out of a flow of thousands or tens of thousands of gallons per minute).

Figure 2:
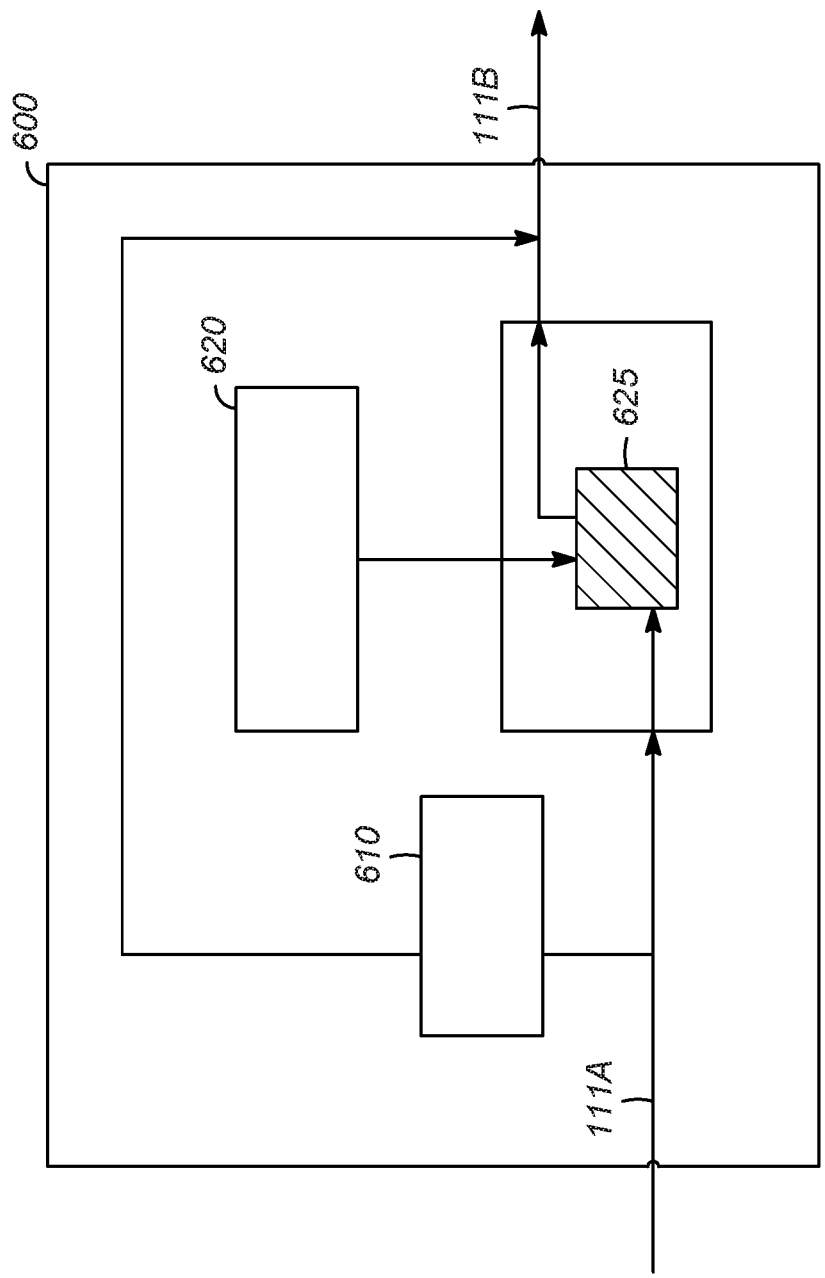
FIG. 2 is a more detailed illustration of the side chamber and analyzer(s) of the present invention.

FIG. 2 shows an analyzer 610 connected to the side chamber 600 for measuring at least one fluid property of the portion 111A of the circulating liquid. In this way, one or more fluid properties can be measured. The fluid properties can include, but are not limited to, the moisture content or the composition (hydrocarbon concentration) of the portion of the pump-around stream. A second moisture sensor 620 can be used to monitor the moisture content of the solid adsorbent 625 inside the side chamber 600. The specific analyzers 610 to be used will depend on the fluid properties being measured and can be determined by those skilled in the art. Suitable analyzers 610 include, but are not limited to, moisture analyzers, gas chromatographs, and spectrometers. When the moisture content on the adsorbent it to be measured, the portion 111A of the pump-around stream is in direct contact with the adsorbent. The adsorbent performance is optimal at a specific hydration concentration with water. This hydration is best measured on the adsorbent where the solid material contacts the process fluid. This measurement will improve the understanding of the adsorbent properties compared to measurements of only the moisture concentration in the bulk process fluid.

After the portion 111A of the circulating liquid passes through the side chamber 600 and the fluid properties have been measured, the return portion 111B may be returned to the conduit 111 from vessel 200 at the pump 210 suction. Alternatively, the return portion 111B can be routed to the outlet of the chamber circulation control valve 630 on conduit 111 at the inlet to vessel 100.

Further application of this technique can be used in the parallel systems of vessel 100 bottoms circulating to vessel 200 by routing a portion 211A from conduit 211 at the pump 110 discharge to side chamber 700. Side chamber 700 will be similar in nature to side chamber 600, although the analyzers used may be different. The return portion 211B will return at the pump 110 suction from vessel 100 or to the inlet of vessel 200 downstream of control valve 730.

The rotary valve is rotated to a plurality of valve positions each of which directs the feed stream to a different one of the sub-beds. In some embodiments, the at least one fluid property is measured at each valve position. In other embodiments, the at least one fluid property is not measured at each valve position. In some embodiments, one fluid property could be measured at each position, while another property would not be measured at every position. Those of skill in the art could determine an appropriate measurement sequence depending on the properties being measured and the needs of the process.

In some embodiments, the number of the plurality of valve positions corresponds to a number of the plurality of sub-beds, wherein the number of the plurality of valve positions is 24 defining a full valve cycle, and wherein rotating the rotary valve comprises rotating the rotary valve for the full valve cycle, and measuring the at least one fluid property is repeated until the full valve cycle is completed.

The claimed process can be used in the process of separating specific $C_8$ aromatics from a feed stream comprising a mixture of $C_8$ aromatics. For example, in some embodiments, the selectively adsorbed component may comprise para-xylene; in others, it could be meta-xylene.

Specific Embodiments

While the following is described in conjunction with specific embodiments, it will be understood that this description is intended to illustrate and not limit the scope of the preceding description and the appended claims.

A first embodiment of the invention is a process for analyzing fluid properties of a stream comprising providing a simulated moving bed system comprising a plurality of adsorbent sub-beds in fluid communication with each other and with a rotary valve for separating one or more selectively adsorbed components from a feed stream comprising the one or more selectively adsorbed components and one or more non-selectively adsorbed components; rotating the rotary valve to a first valve position to direct the feed stream to a first sub-bed of the plurality of sub-beds; introducing a portion of a pump-around stream between two of the adsorbent sub-beds into a side chamber comprising an adsorbent; measuring a moisture content of the adsorbent in the side chamber or at least one fluid property of the portion of the pump-around stream in the side chamber or both using an analyzer. An embodiment of the invention is one, any or all of prior embodiments in this paragraph up through the first embodiment in this paragraph wherein the at least one fluid property comprises at least one of a moisture content of the pump-around stream, a composition of the pump-around stream, or a concentration of a hydrocarbon species of the pump-around stream. An embodiment of the invention is one, any or all of prior embodiments in this paragraph up through the first embodiment in this paragraph wherein the at least one fluid property is the composition of the portion of the pump-around stream and wherein the analyzer is a gas chromatograph. An embodiment of the invention is one, any or all of prior embodiments in this paragraph up through the first embodiment in this paragraph wherein the at least one fluid property is the concentration of a hydrocarbon species in the portion of the pump-around stream and wherein the analyzer comprises a spectrometer. An embodiment of the invention is one, any or all of prior embodiments in this paragraph up through the first embodiment in this paragraph wherein the at least one fluid property is the moisture content of the pump-around stream and wherein the analyzer comprises a moisture analyzer. An embodiment of the invention is one, any or all of prior embodiments in this paragraph up through the first embodiment in this paragraph wherein the moisture content of the adsorbent is measured and wherein the portion of the pump-around stream is in direct contact with the adsorbent. An embodiment of the invention is one, any or all of prior embodiments in this paragraph up through the first embodiment in this paragraph wherein the analyzer is a moisture analyzer. An embodiment of the invention is one, any or all of prior embodiments in this paragraph up through the first embodiment in this paragraph further comprising returning the portion of the pump-around stream from the side chamber to a remainder of the pump-around stream after measuring the at least one fluid property. An embodiment of the invention is one, any or all of prior embodiments in this paragraph up through the first embodiment in this paragraph wherein the feed stream comprises $C_8$ aromatics and the selectively adsorbed component comprises para-xylene. An embodiment of the invention is one, any or all of prior embodiments in this paragraph up through the first embodiment in this paragraph wherein rotating the rotary valve comprises rotating the rotary valve to a plurality of valve positions that each direct the feed stream to a different one of the sub-beds, and measuring the at least one fluid property is repeated for each of the plurality of valve positions to assess the at least one fluid property at each valve position. An embodiment of the invention is one, any or all of prior embodiments in this paragraph up through the first embodiment in this paragraph wherein a number of the plurality of valve positions corresponds to a number of the plurality of sub-beds, wherein the number of the plurality of valve positions is 24 defining a full valve cycle, and wherein rotating the rotary valve comprises rotating the rotary valve for the full valve cycle, and measuring the at least one fluid property is repeated until the full valve cycle is completed.

A second embodiment of the invention is a process for analyzing fluid properties of a stream comprising providing a simulated moving bed system comprising a plurality of adsorbent sub-beds in fluid communication with each other and with a rotary valve for separating one or more selectively adsorbed components from a feed stream comprising the one or more selectively adsorbed components and one or more non-adsorbed components; rotating the rotary valve to a first valve position to direct the feed stream to a first sub-bed of the plurality of sub-beds; introducing a portion of a pump-around stream between two of the adsorbent sub-beds into a side chamber comprising an adsorbent and wherein the portion of the pump-around stream is in direct contact with the adsorbent; measuring a moisture content of the adsorbent using a moisture analyzer. An embodiment of the invention is one, any or all of prior embodiments in this paragraph up through the second embodiment in this paragraph further comprising measuring at least one additional fluid property of the portion of the pump-around stream. An embodiment of the invention is one, any or all of prior embodiments in this paragraph up through the second embodiment in this paragraph wherein the at least one additional fluid property comprises at least one of a moisture content of the pump-around stream, a composition of the pump-around stream, or a concentration of a hydrocarbon species of the pump-around stream. An embodiment of the invention is one, any or all of prior embodiments in this paragraph up through the second embodiment in this paragraph further comprising returning the portion of the pump-around stream from the side chamber to a remainder of the pump-around stream after measuring the property. An embodiment of the invention is one, any or all of prior embodiments in this paragraph up through the second embodiment in this paragraph wherein the feed stream comprises $C_8$ aromatics and the selectively adsorbed component comprises para-xylene. An embodiment of the invention is one, any or all of prior embodiments in this paragraph up through the second embodiment in this paragraph wherein rotating the rotary valve comprises rotating the rotary valve to a plurality of valve positions that each direct the feed stream to a different one of the sub-beds, and measuring the at least one fluid property is repeated for each of the plurality of valve positions to assess the at least one fluid property at each valve position.

A third embodiment of the invention is an apparatus for separating one or more selectively adsorbed components from a feed stream comprising the selectively adsorbed component and one or more non-selectively adsorbed components, the system comprising a plurality of adsorbent sub-beds in fluid communication with each other and comprising two sub-beds in direct fluid communication with each other via a pump-around stream; a rotary valve in fluid communication with each of the plurality of sub-beds and configured to rotate to a plurality of valve positions that each direct the feed stream to a different one of the plurality of sub-beds; a side chamber in fluid communication with the pump-around stream; and an analyzer for a property in communication with the side chamber. An embodiment of the invention is one, any or all of prior embodiments in this paragraph up through the third embodiment in this paragraph wherein the analyzer is selected from a moisture analyzer, a gas chromatograph, or a spectrometer. An embodiment of the invention is one, any or all of prior embodiments in this paragraph up through the third embodiment in this paragraph wherein there are at least two analyzers in the side chamber Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for analyzing fluid properties of a stream comprising:
   providing a simulated moving bed system comprising a plurality of adsorbent sub-beds in fluid communication with each other and with a rotary valve for separating one or more selectively adsorbed components from a feed stream comprising the one or more selectively adsorbed components and one or more non-selectively adsorbed components;
   rotating the rotary valve to a first valve position to direct the feed stream to a first sub-bed of the plurality of sub-beds;
   introducing a portion of a pump-around stream between two of the adsorbent sub-beds into a side chamber comprising an adsorbent;
   measuring a moisture content of the adsorbent in the side chamber or at least one fluid property of the portion of the pump-around stream in the side chamber or both using an analyzer.

2. The process of claim 1 wherein the at least one fluid property comprises at least one of: a moisture content of the pump-around stream, a composition of the pump-around stream, or a concentration of a hydrocarbon species of the pump-around stream.

3. The process of claim 2 wherein the at least one fluid property is the composition of the portion of the pump-around stream and wherein the analyzer is a gas chromatograph.

4. The process of claim 2 wherein the at least one fluid property is the concentration of a hydrocarbon species in the portion of the pump-around stream and wherein the analyzer comprises a spectrometer.

5. The process of claim 2 wherein the at least one fluid property is the moisture content of the pump-around stream and wherein the analyzer comprises a moisture analyzer.

6. The process of claim 1 wherein the moisture content of the adsorbent is measured and wherein the portion of the pump-around stream is in direct contact with the adsorbent.

7. The process of claim 6 wherein the analyzer is a moisture analyzer.

8. The process of claim 1 further comprising:
   returning the portion of the pump-around stream from the side chamber to a remainder of the pump-around stream after measuring the at least one fluid property.

9. The process of claim 1 wherein the feed stream comprises $C_8$ aromatics and the selectively adsorbed component comprises para-xylene.

10. The process of claim 1 wherein rotating the rotary valve comprises rotating the rotary valve to a plurality of valve positions that each direct the feed stream to a different one of the sub-beds, and measuring the at least one fluid property is repeated for each of the plurality of valve positions to assess the at least one fluid property at each valve position.

11. The process of claim 10 wherein a number of the plurality of valve positions corresponds to a number of the plurality of sub-beds, wherein the number of the plurality of valve positions is 24 defining a full valve cycle, and wherein rotating the rotary valve comprises rotating the rotary valve for the full valve cycle, and measuring the at least one fluid property is repeated until the full valve cycle is completed.

12. A process for analyzing fluid properties of a stream comprising:
   providing a simulated moving bed system comprising a plurality of adsorbent sub-beds in fluid communication with each other and with a rotary valve for separating one or more selectively adsorbed components from a feed stream comprising the one or more selectively adsorbed components and one or more non-adsorbed components;
   rotating the rotary valve to a first valve position to direct the feed stream to a first sub-bed of the plurality of sub-beds;
   introducing a portion of a pump-around stream between two of the adsorbent sub-beds into a side chamber comprising an adsorbent and wherein the portion of the pump-around stream is in direct contact with the adsorbent;
   measuring a moisture content of the adsorbent using a moisture analyzer.

13. The process of claim 12 further comprising:
   measuring at least one additional fluid property of the portion of the pump-around stream.

14. The process of claim 13 wherein the at least one additional fluid property comprises at least one of: a moisture content of the pump-around stream, a composition of the pump-around stream, or a concentration of a hydrocarbon species of the pump-around stream.

15. The process of claim 12 further comprising:
   returning the portion of the pump-around stream from the side chamber to a remainder of the pump-around stream after measuring the property.

16. The process of claim 12 wherein the feed stream comprises $C_8$ aromatics and the selectively adsorbed component comprises para-xylene.

17. The process of claim 12 wherein rotating the rotary valve comprises rotating the rotary valve to a plurality of valve positions that each direct the feed stream to a different one of the sub-beds, and measuring the at least one fluid property is repeated for each of the plurality of valve positions to assess the at least one fluid property at each valve position.

\* \* \* \* \*